United States Patent [19]

Polaschegg

[11] Patent Number: 5,100,554
[45] Date of Patent: Mar. 31, 1992

[54] METHOD FOR THE IN-VIVO DETERMINATION OF HEMODIALYSIS PARAMETERS

[75] Inventor: Hans-Dietrich Polaschegg, Oberursel, Fed. Rep. of Germany

[73] Assignee: Fresenius AG, Fed. Rep. of Germany

[21] Appl. No.: 615,450

[22] Filed: Nov. 19, 1990

[30] Foreign Application Priority Data

Nov. 21, 1989 [DE] Fed. Rep. of Germany ....... 3938662

[51] Int. Cl.$^5$ .............................................. B01D 61/32
[52] U.S. Cl. .................................. 210/647; 210/96.2; 210/746; 210/646
[58] Field of Search .............. 210/647, 646, 746, 96.2; 604/4, 5, 6

[56] References Cited

U.S. PATENT DOCUMENTS

| | | | |
|---|---|---|---|
| 4,508,622 | 4/1985 | Polaschegg et al. | 210/96.2 |
| 4,668,400 | 5/1987 | Veech | 210/647 |
| 4,923,613 | 5/1990 | Chevallet | 210/647 |
| 5,024,756 | 6/1991 | Sternby | 210/647 |

FOREIGN PATENT DOCUMENTS 3640089  6/1988  Fed. Rep. of Germany .

*Primary Examiner*—W. Gary Jones
*Attorney, Agent, or Firm*—Marshall, O'Toole, Gerstein, Murray & Bicknell

[57] ABSTRACT

This invention relates to a method for the in-vivo determination of hemodialysis parameters. To carry out hemodialysis with the greatest efficiency and safety, it is inter alia necessary to know the clearance of the dialyzer. To be able to determine the same in vivo, the invention provides a method in which the electrolyte transfer of the dialysis fluid is measured by means of a measuring device at two different predetermined dialysis fluid ion concentrations and the dialysance is determined on the basis thereof, which dialysance is numerically equal to the clearance.

9 Claims, No Drawings

METHOD FOR THE IN-VIVO DETERMINATION OF HEMODIALYSIS PARAMETERS

BACKGROUND OF THE INVENTION

This invention relates to a method for the in-vivo determination of hemodialysis parameters using an apparatus for adjusting the ion concentration of the dialysis fluid and a measuring device.

For many years hemodialysis has been used for treating patients and has proved successful all over the world. Although the hemodialysis technology has reached an advanced stage, there are some important aspects by reason of which hemodialysis methods are in need of development. In particular the financial costs for the long-term treatment of patients suffering from chronic diseases plays an important role. Due to the rising costs in the health systems of the industrialized countries and the financial problems in the developing countries, it is necessary to further reduce the hemodialysis costs to be able to treat a still increasing number of patients. The cost factor of hemodialysis treatments largely depends on whether the method can be carried out in an optimum way. On the one hand the treatment time can be shortened when the method is optimally performed and, on the other hand, the additional nursing costs incurred by a patient who is well tended thanks to an optimum hemodialysis treatment are reduced due to the fact that the patient is less morbid and therefore needs less care.

Within the NCCLS (National Committee for Clinical and Laboratory Standards) the morbidity of a large group of patients was examined in the United States in response to the dialysis dose. It turned out that the morbidity falls to a low constant value when the value for K t/V rises from 0.8 to 1 or more.

K is here the clearance, t the treatment time and V the whole body water of a patient. It is therefore desirable to control each treatment in such a way that K t/V becomes 1 for each treatment.

For an optimum hemodialysis, and for avoiding an increase in the morbidity, it is thus imperative to either exactly determine the above-mentioned ratio K t/V or to increase the dialysis time for reasons of safety. Apart from possible health risks, the latter entails considerable costs. To optimize hemodialysis, the patient's whole body water V may be determined, which can be done in a relatively easy way as the same is known over a long period. The whole body water can be deduced from the patient's body weight, his age and sex and the estimated fat portion. It can also be calculated on the basis of urea measurements and with the aid of the urea model. In addition, a whole body impedance measurement can be carried out for the purpose of determination. Furthermore, it is relatively easy to determine the treatment time t for the respective treatment of a patient.

By contrast, the prior art does not disclose any methods which could be employed in vivo for exactly determining the clearance of a hemodialyzer. As a rule, the details given by the manufacturer are taken as a basis. These details, however, include considerable errors. For instance, the manufacturer does not check each single dialyzer as to its clearance. Rather, the manufacturer guarantees a specific clearance range, which however does not exclude the possibility that some dialzyers do not comply with this range.

Another reason for changes in the clearance is that dialyzers are reconditioned and reused, above all in the United States, for reasons of costs and biocompatibility.

Another reason why the information given by the manufacturer about the clearance cannot be fully relied on is that the manufacturer's information is based on measurements in aqueous solutions, while the relevant clearance during the treatment of a patient relates to the aqueous portion of blood. The flow of this aqueous amount is calculated from the entire blood flow and the hematocrit of a patient. Although the hematocrit is normally known, it may vary during hemodialysis due to ultrafiltration.

In addition, it must be taken into account that the blood flow is only approximately known, as it normally depends on the delivery rate, i.e. the rotational speed of a conventionally used peristaltic blood pump and the flexible tube diameter of the system. Since the tube diameter is only known at an accuracy of $+/- 5\%$, and since, moreover, the cross-section of the pump may be reduced due to the suction vacuum, considerable tolerances result therefrom.

It follows from the above that it has not been possible in the prior art to measure the clearance in vivo and that the formerly known calculation methods have been subject to considerable inaccuracies.

To overcome these problems, in-vivo urea measurements are carried out in the prior art, as the relevant clearance of the dialyzer is the urea clearance and the above-mentioned calculation formula is based on the urea model. For urea measurements samples must be taken and examined in the laboratory. As a result, there are considerable time delays between the taking of the samples and the availability of the measurement results. The dialysis treatment can thus not be controlled. Furthermore, these examinations are very expensive. As a rule, the patient is therefore treated on the basis of estimated values and a margin of safety, a quality control being only carried out at greater time intervals, e.g. once a month, through urea measurements.

Furthermore, it is known from the prior art that the clearance for sodium chloride ions is equal to the urea clearance. Since the ion concentration and thus the conductivity of the dialysis fluid and of blood substantially depend on Na and Cl ions, it is possible to determine the clearance through a conductivity measurement. In a known method the concentration is given at the blood inlet side of the hemodialyzer and set to zero at the dialysis fluid inlet side, or vice versa, for determining the clearance. However, this method has the disadvantage that during the dialysis process it is not possible to set the inlet concentration at the dialysis fluid inlet side to zero. Furthermore, the inlet concentration of blood is not known. Hence, this method is not suited for an in-vivo control of the hemodialysis process.

OBJECT UNDERLYING THE INVENTION

It is the object of this invention to provide a method of the above-mentioned type by which hemodialysis parameters can be determined, in particular the clearance of a dialyzer, and which permits an in-vivo measurement of the parameters in a simple and reliable way without the need for any large or expensive technical equipment.

INVENTIVE SOLUTION

In accordance with the invention, this object is attained in that the electrolyte transfer of the dialysis fluid is measured by a measuring device at two different predetermined dialysis fluid ion concentrations and that the dialysance is determined on the basis threof.

DESCRIPTION OF THE INVENTION

The method of the invention offers a number of considerable advantages. In accordance with the invention, it is e.g. possible to determine the corresponding measurement values with the aid of a means which is of a simple construction and can be operated in a reliable way. This means may e.g. be the one described in German patent No. 32 23 051 and its U.S. counterpart (Polaschegg, et al. U.S. Pat. No. 4,508,622 issued Apr. 2, 1985), the disclosure which which is incorporated herein by reference. It is thereby possible to measure the Na ion concentration and the conductivity, respectively, upstream or downstream of the dialyzer in the dialysis fluid.

It has been found to be especially advantageous when, in accordance with the invention the measurement is carried out at two different predetermined ion concentrations which can be adjusted accordingly. It is thus possible to adjust these concentrations to physiologically reasonable values without the hemodialysis process being impaired or disturbed thereby. An advantage of the invention must be seen in the fact that the two different concentration values to be adjusted can be adjusted within a very short period of a few minutes. It can consequently be assumed that rhe blood concentration Cbi and the dialysance D do not vary within said period.

Since in accordance with the invention the incoming dialysis fluid already comprises a specific inlet concentration, it is possible to set up the equation for the dialysance as shown hereinafter. As for the calculation basis, reference is made to Sargent, J. A., Gotch, F. A : Principles and biophysics of dialysis, in: Replacement of Renal Function by Dialysis, W. Drukker, F. M.Parsons, J. F. Maher (ed.), Nijhoff, The Hague, 1983.

$$D = Qb \cdot \frac{Cbi - Cbo}{Cbi - Cdi} \quad (1)$$

For reasons of mass balance there is
ti $Qb \cdot (Cbi - Cbo) =$
$-Qd \cdot (Cdi - Cdo)$ \quad (2)

It follows from the two above-mentioned equations (1) and (2):

$$D = -Qd \cdot \frac{Cdi - Cdo}{Cbi - Cdi} \quad (3)$$

where:
Cbi: blood inlet concentration
Cbo: Blood outlet concentration
Qb : blood flow
D : dialysance
Cdi: dialysis fluid inlet concentration
Cdo: dialysis fluid outlet concentration
Qd : dialysis fluid flow Since Qd and Cdi are given and the value Cdo is measured, only D and Cbi are unknown in the above-mentioned equations. Hence, in accordance with the invention, there are two equations with two unknown variables which can be calculated as follows:

$$D = Qd \cdot \frac{(Cdi1 - Cdo1) - (Cdi2 - Cdo2)}{Cdi1 - Cdi2} \quad (4)$$

With the aid of equation (4) the dialysance can be determined by using the method of the invention. Its numerical value is identical with the hemodialyzer clearance to be found.

Indices 1 and 2 stated in equation (4) relate to the first adjustment and second adjustment, respectively, of the dialysis fluid concentration.

In an especially advantageous embodiment of the invention, the two measurements are carried out at a short time interval. This ensures that the other parameters do normally not vary anymore and can thus be considered to be constant.

In an especially advantageous embodiment of the invention, the sodium ion concentration of the dialysis fluid is measured. Alternatively, it is also possible to determine the temperature-corrected conductivity of the dialysis fluid, this operation being preferably carried out with the aid of a conductivity sensor.

In accordance with the invention, the measured values are advantageously evaluated according to the above-mentioned equation (4), which has the advantage that the blood concentration does not appear in the equation as a numerical value.

In addition to the pure dialysis process, the method of the invention is also applicable to dialysis with ultrafiltration; it is possible to carry out the measurement even if the ultrafiltration process has been stopped. If the result of the determination method of the invention can be used for predetermining the necessary dialysis time, any correction of the measurement results can be dispensed with, i.e. the result obtained through equation (4), which implicitly includes the ultrafiltration impact, can directly be used.

With the method of the invention it is possible to detect a change in the patient's blood volume. As is generally known, such a change in the blood volume leads to an increase in the hematocrit and a decrease in the aqueous portion of blood. Since the clearance and the dialysance, respectively, relate to the aqueous portion of blood, the same decrease with a decreasing aqueous portion of blood. The reason for this must be seen in the fact that the explanations given above apply, strictly speaking, to aqueous solutions only, while equation (4) also applies to blood, as the blood concentration of the equation is eliminated.

The blood inlet concentration Cbi can be determined from the above derivation for aqueous solutions only. With blood, however, it is necessary to take the Gibbs-Donnan coefficient into account. Blood concentration thus means the concentration in the aqueous phase of blood which is e.g. determined by an ionometer. The blood inlet concentration Cbi can be represented in the following way:

$$Cbi = \frac{Cdi}{\alpha}, \quad (5)$$

where ($\alpha$) is the so-called Gibbs-Donnan coefficient.
According to Sargent and Gotch the coefficent $$\alpha = 1 - 0.0074 \, Ctp \quad (6)$$

where Ctp is the plasma protein concentration measured in (g/dl).

If the plasma protein concentration or its value is known, the blood concentration is as follows in consideration of equations (1-6):

$$Cbi(a) = Cdi - \frac{Qd}{D}(Cdi - Cdo) \qquad (7)$$

If in accordance with the invention the quotient of the measured dialysance (clearance) and the blood flow is followed, the change in the blood volume can be inferred therefrom. However, a precondition is that the transportation properties of the dialysis membrane remain unchanged, i.e. the membrane will not be blocked in part. Such disorders during hemodialysis can however be detected by suitable detectors.

Furthermore, the method of the invention has the advantage that changes in the transportation properties of the membrane can be inferred if there are other methods for determining the change in the blood volume. Hence, changes in the transportation property of the membrane can be determined on the basis of a comparison made between the calculated changes in the clearance and the measured change.

To be able to determine the dependance of the parameters on the dialysis fluid flow with the aid of the method of the invention, the dialysis fluid flow can be variably adjusted to different values in another embodiment of the invention, so that according to equation (4) the dialysance can be determined in dependance upon the dialysis fluid flow. Hence, it is possible to determine that dialysis fluid flow where e.g. a specific percentage of the dialysance will be reached at a given dialysis fluid flow, e.g. 1000 ml/min or $Qd = 2 Qb$. Hence, it is possible by using the method of the invention to adjust a dialysis fluid flow in the case of which the patient can be treated in a particularly inexpensive way.

The present invention is not to be understood as restricted to the embodiments and applications shown. Rather, many modifications are possible without departing from the spirit and scope of the invention, in particular with respect to the variation of the corresponding parameters.

I claim:

1. A method for the in-vivo determination of hemodialysis parameters with a dialyzer using an apparatus for adjusting the ion concentration of the dialysis fluid and a measuring device, comprising measuring the electrolyte transfer of said dialysis fluid by making first and second measurements with said measuring device at two different predetermined dialysis fluid ion concentrations and determining the dialysance by determining the difference between the differences of said dialysis fluid ion concentration at the inlet side and the outlet side of the dialyzer at the time of the first and second measurements, respectively, dividing the result by the difference of said dialysis fluid ion concentration at said inlet side at the time of said first and said second measurements, and multiplying by the dialysis fluid flow.

2. A method according to claim 1, comprising carrying out the two measurements at a short time intervals.

3. A method according to claim 1 or 2 comprising measuring the Na concentration of said dialysis fluid.

4. A method according to claim 1 or 2, comprising measuring the temperature-corrected conductivity of said dialysis fluid.

5. A method according to claim 1, comprising carrying out the measurements by using conductivity sensors.

6. A method according to claim 1, comprising determining the clearance of said dialyzer on the basis of said determined dialysance.

7. A method according to claim 1, comprising determining changes in the aqueous portion of blood by measuring changes in one or both of said clearance and said dialysance.

8. A method according to claim 1, comprising determining changes in the blood volume and comparing said changes with changes in one or both of said clearance and said dialysance, and determining changes in the transportation properties of the membrane on the basis thereof.

9. A method according to claim 1, comprising adjusting said dialysis fluid flow to two different values and determining said dialysance in dependence upon said dialysis fluid flow.

* * * * *